United States Patent
Chou (10) Patent No.: US 12,208,944 B2
(45) Date of Patent: Jan. 28, 2025

(54) DISPENSER FOR DISPENSING GLOVES CUFF-FIRST

(71) Applicants: BERGAMOT SDN. BHD., Selangor (MY); Miew Fatt Chou, Selangor (MY)

(72) Inventor: Miew Fatt Chou, Petaling Jaya (MY)

(73) Assignees: BERGAMOT SDN. BHD, Selangor (MY); Miew Fatt Chou, Selangor (MY)

( * ) Notice: Subject to any disclaimer, the term of this patent is extended or adjusted under 35 U.S.C. 154(b) by 569 days.

(21) Appl. No.: 17/283,526

(22) PCT Filed: Nov. 12, 2019

(86) PCT No.: PCT/MY2019/050087
§ 371 (c)(1),
(2) Date: Apr. 7, 2021

(87) PCT Pub. No.: WO2020/101473
PCT Pub. Date: May 22, 2020

(65) Prior Publication Data
US 2021/0387766 A1 Dec. 16, 2021

(30) Foreign Application Priority Data
Nov. 12, 2018 (MY) .............................. 2018704235

(51) Int. Cl.
*B65D 5/54* (2006.01)
*B65D 83/08* (2006.01)

(52) U.S. Cl.
CPC ........... *B65D 5/54* (2013.01); *B65D 83/0805* (2013.01); *B65D 83/0894* (2013.01)

(58) Field of Classification Search
CPC ... B65D 5/54; B65D 83/0805; B65D 85/0894
See application file for complete search history.

(56) References Cited

U.S. PATENT DOCUMENTS

| | | | | |
|---|---|---|---|---|
| 2,501,357 A | * | 3/1950 | Speckman | B65D 83/0852 221/56 |
| 3,243,079 A | * | 3/1966 | Rettmer | B65D 83/0811 221/63 |
| 5,816,440 A | * | 10/1998 | Shields | A61B 42/40 221/45 |
| 6,648,172 B2 | * | 11/2003 | Leighton | A47K 10/424 221/48 |

(Continued)

FOREIGN PATENT DOCUMENTS

JP 05 055987 U 7/1993
JP 3202591 U 2/2016

*Primary Examiner* — Tri M Mai
(74) *Attorney, Agent, or Firm* — Craft Chu PLLC; Andrew W. Chu (57) ABSTRACT

A dispenser for disposable gloves includes a box having a plurality of faces, and two stacks of unfolded gloves disposed in the box and a static internal separator positioned between each stack of gloves. The box has 5 perforated lines on at least two opposing faces. The perforated lines are tearable providing a respective dispensing aperture on each opposing face. Each stack of gloves is orientated in the box so that the cuff of the gloves is positioned adjacent to the dispensing aperture for dispensing cuff-first through said dispensing aperture.

9 Claims, 4 Drawing Sheets

(56) References Cited

U.S. PATENT DOCUMENTS

| | | | |
|---|---|---|---|
| 2002/0125264 A1* | 9/2002 | Shiffler | B65D 83/0805 |
| | | | 221/47 |
| 2003/0226851 A1* | 12/2003 | Antebi | B65D 5/48024 |
| | | | 221/47 |
| 2004/0182874 A1 | 9/2004 | Kringel et al. | |
| 2007/0215628 A1 | 9/2007 | Tramontina | |
| 2018/0105348 A1 | 4/2018 | Modha et al. | |
| 2018/0111744 A1* | 4/2018 | Modha | B65D 85/18 |

* cited by examiner

DISPENSER FOR DISPENSING GLOVES CUFF-FIRST

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This invention relates to a dispenser adapted to hold and dispense a plurality of gloves. More particularly, the invention relates to a dispenser adapted to hold and dispense a plurality of gloves cuff-first.

2. Description of Related Art Including Information Disclosed Under 37 CFR 1.97 and 37 CFR 1.98

Most gloves used in hospitals and clinics are examination gloves, and these are used in large numbers. Such gloves are supplied not in individual sterile packages, but in relatively inexpensive cardboard dispensing boxes. The dispenser typically consists of quantities of gloves that are contained in a corrugated box with a perforated region. When the perforated region is removed, an opening is provided through which gloves are withdrawn by a user.

In a dispenser which dispenses gloves that are in vertical position, one or more portions of gloves often protrude through the opening when the dispensing box is nearly or completely filled with a plurality of gloves. When the dispensing box is completely or nearly full, it can be difficult for a user to grasp one glove without causing inadvertent dispensing of additional gloves.

Once the first 10 to 20 percent of the gloves are dispensed, a space between the opening and the plurality of gloves is created. This space requires a user to place a portion of his/her hand into the opening to grasp a glove. As this space increases when more of the gloves are dispensed from the dispenser, the gloves have a tendency to collapse from their dispensing position and to clump together at the bottom of the dispenser. This results in a user having to place his/her hand deep into the dispenser to dispense a single glove.

In a dispenser which dispenses gloves that are in horizontal position, the same problems occur when the dispenser is nearly or completely full of gloves. Again, once the first 10-20 percent of gloves are dispensed, the user is required to place his/her hand into the opening of the dispenser to retrieve a glove. While clumping may not occur, the continued admittance of user hands into a dispenser opening may result in contamination of one or more gloves, or the entire internal compartment of the dispenser and most or all of the plurality of gloves.

One way of controlling contamination on such examination gloves is by packaging the gloves with over-folded cuffs within a box having a dispensing aperture. Since the gloves are folded, there is less surface area to contaminate.

US 2011/0062179 relates to the dispensing of gloves from a dispenser, the dispenser comprising a container and a plurality of disposable gloves. The container has a plurality of faces, and each glove has a cuff portion and a finger portion, the cuff portion having a cuff and the gloves being stacked one on another with the cuffs of the gloves being aligned on one side of the stack of gloves held within the container. The container has in use a dispensing aperture in at least one face of the container through which gloves can be dispensed. The gloves are oriented in the container so that the gloves are positioned for dispensing cuff-first through the aperture, and the finger portion of each glove is folded back against the cuff portion of the same glove to protect the finger portion from user contact and contamination during dispensing of the glove. The dispensing aperture includes a portion of the aperture that extends across a portion of a face. However, the manufacturing process is complex due to the additional machinery required to fold and overlap the gloves.

EP 2 004 519 B1 discloses a dispensing assembly which includes a dispenser having a housing comprising a plurality of walls which cooperate to form an inner surface and an internal compartment. The dispenser is configured to hold a stack of gloves and a stack of gloves is disposed in the dispenser. The dispenser includes a pair of spaced-apart dispensing openings. The stack of gloves is positioned on a glove positioner having a pair of opposing ends such that gloves are positioned in a stack cuff-to-cuff at each end of the glove positioner which positions each cuff of a glove adjacent one of the dispensing openings. A first glove positioner includes a resilient material which biases the first stack of gloves toward the dispensing opening. A second glove positioner includes a resilient material which biases the second stack of gloves toward the dispensing opening. The stack of gloves is biased against the dispensing openings to permit easy and reliable withdrawal of each glove therefrom. However, additional components such as the resilient material would be required, increasing manufacturing costs. Further the manufacturing process is complex due to the additional components that need to be assembled.

GB 2 451 450 A discloses a dispenser for dispensing disposable gloves from a container in which they are packed as a stack of gloves lying all in the same orientation and unfolded with the cuffs of the gloves being aligned on one side of the stack of gloves. The container has a dispensing aperture in one face of the container through which the gloves can be dispensed. The aperture extends up to an edge of the face, but not beyond the edge of the face. A plate bears on the bottom of the stack of gloves, and a spring pushes the stack up in the box towards the dispensing aperture. However, additional components such as the plate and springs would be required, increasing manufacturing costs. Further the manufacturing process is complex due to the amount of components that need to be assembled.

Accordingly, there is a need for a dispenser for disposable gloves which is configured to hold and dispense a plurality of gloves cuff-first without incurring additional manufacturing costs or processes. Such a dispenser assembly desirably permits a plurality of gloves to be easily dispensed one at a time. In addition, the opening to the dispenser is desirably configured and positioned such that minimal surface area of the glove adjacent the opening is exposed.

BRIEF SUMMARY OF THE INVENTION

In accordance with an aspect of the invention, there is provided a dispenser for gloves that comprises:
- a box having a plurality of faces, the box having perforated lines on at least two opposing faces, where said perforated lines are tearable providing a respective dispensing aperture on each opposing face;
- two stacks of unfolded gloves disposed in the box, where each stack of gloves is orientated in the box so that the cuff of the gloves are positioned adjacent to the dispensing aperture; and
- a static internal separator positioned between each stack of gloves.

The invention thus allows the gloves to be for dispensed cuff-first through a respective dispensing aperture preventing contamination of one or more gloves. Further, as the finger portions of the gloves are not exposed prior to dispensing, any contamination from the user upon touching the glove for dispensing is limited to the cuff portion of the glove. The manufacturing process is simplified as no additional components such as plates and springs would need to be assembled.

The static internal separator according to the invention allows two stacks of gloves to be disposed in the box permitting dispensing of the gloves from two opposing apertures.

In a preferred embodiment of the invention, the gloves in each stack are stacked unfolded one on another cuff-to-cuff and the dispenser is arranged in use to dispense the glove from one aperture. Once gloves have been dispensed from one stack of gloves, the box is turned upside-down for dispensing of the gloves from the opposing aperture.

The unfolded arrangement of the gloves according to the invention provides the benefit of where the user does not have to place his/her hand deep into the dispenser to dispense a single glove as there is less space between the top of the glove and the aperture, as compared to when gloves are stacked folded.

In an embodiment, the static internal separator is a single sheet element having end tabs used to support the separator within the box.

In a preferred embodiment, the sheet element comprises a gradient portion between the end tabs. The invention thus allows the gloves to slide cuff out first and also prevents the gloves from moving backwards when a glove is withdrawn. Since the cuff of each glove is often thicker, the gradient portion allows for a stack of gloves on each side of the separator and each stack is generally trapezoidal in shape. The problem previously caused due to an asymmetry of a stack of gloves stacked cuff-to-cuff is solved by using the trapezoidal cross-section of the stacks of gloves to fill a rectangular dispenser, thereby removing or controlling unwanted space which results from the asymmetry and from dispensing and depleting the gloves from the dispenser.

In a further embodiment, the sheet element further comprises a flat portion for placement of the cuff of the gloves, where the flat portion is disposed between the gradient portion and the flat portions. The flat portion according to the invention is used to support the cuffs of the gloves.

In an embodiment, the sheet element comprises fold lines between the gradient portion and the flat portion.

In another embodiment, the end tabs of the sheet element are bent in opposing directions.

In an embodiment, the end tabs of the sheet element are positioned parallel to the opposing faces such that the end tabs come in contact with the opposing faces. This allows the cuffs of the gloves to be supported.

In a further embodiment, the box has a further set of tearable perforated lines adjoining the perforated lines to extend the aperture to an adjoining face. The invention thus allows the gloves to be easily dispensed cuff-first through a dispensing aperture.

In an embodiment, the perforated lines define a flap having a closed position and an open position to close or open the dispensing aperture. Thus, the flap shields the dispensing aperture from the entry of contaminants into the box from the surrounding environment.

In another embodiment, the static internal separator is two sheet elements, each sheet element having a flat portion for receiving a respective stack of gloves and side tabs used to support the sheet elements within the box.

In a preferred embodiment, the flat portions of each sheet elements are disposed on one another.

In a further embodiment, the side tabs of the separator are positioned parallel to the side faces of the box. This allows the gloves to be supported.

In an embodiment, the dispensing aperture is covered by a film having a slit for each glove to pass through. Thus, the film shields the dispensing aperture from the entry of contaminants into the box from the surrounding environment.

Additional advantages of the dispenser for gloves of this invention will be elaborated in the following pages.

DETAILED DESCRIPTION OF THE INVENTION

Figure 1A:
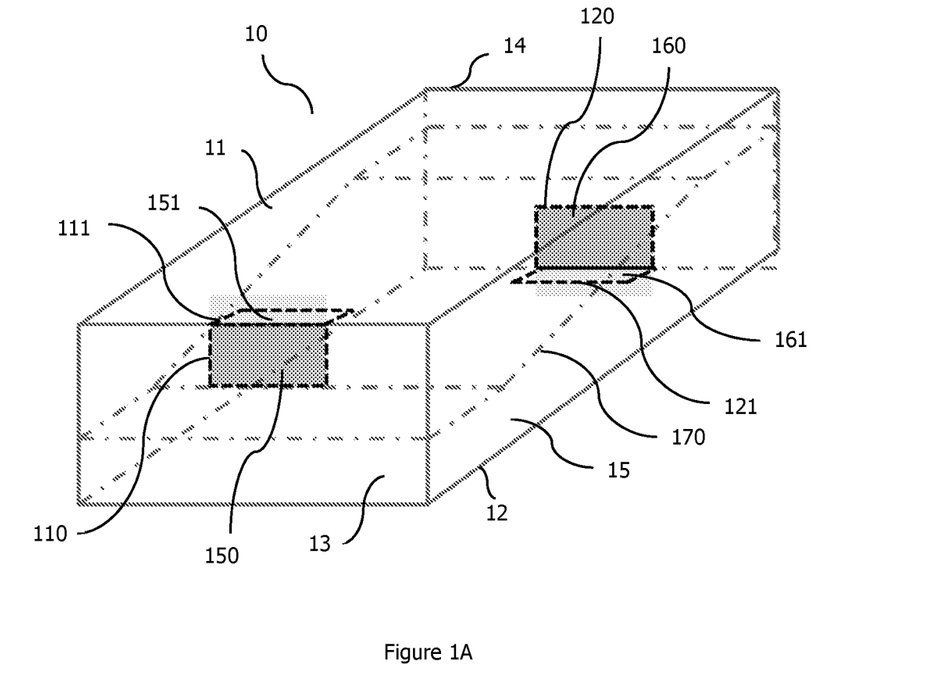
FIG. 1A is a perspective view of a dispenser for dispensing gloves showing a static internal separator and a box having a flap defined by perforations on the front face and back face of the box such that, when opened by tearing, a dispensing aperture is provided.
Figure 1B:
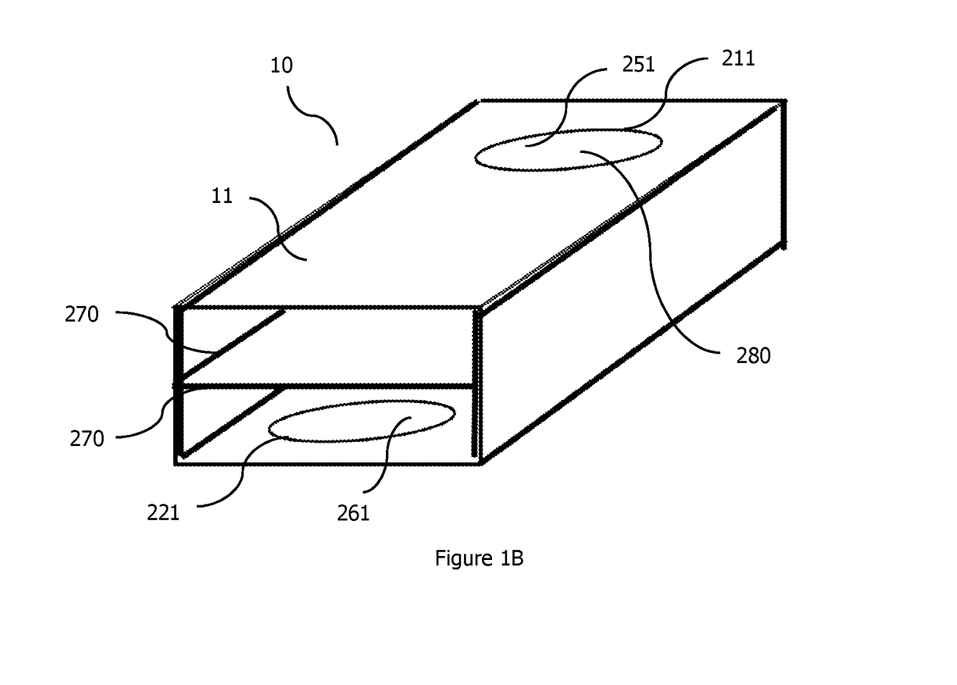
FIG. 1B is a perspective view of a dispenser for dispensing gloves showing a static internal separator and a box having a flap defined by perforations on the upper face and lower face of the box such that, when opened by tearing, a dispensing aperture is provided.

FIGS. 1A and 1B shows a dispenser for dispensing gloves in the form of a box 10 with an upper face 11, lower face 12, front face 13, back face 14 and side faces 15. The width of the box 10 corresponds broadly to the width of a glove laid flat in the box 10 measured from the thumb to the little finger. The length of the box corresponds broadly to the length of a glove laid flat in the box 10 measured from the cuff to the middle finger. The height of the box 10 corresponds broadly to the total height of the gloves in the box 10 measured on its cuff side. Therefore, the side faces 15 have a length greater than the width of the front and back faces 13, 14. Also, in this embodiment, the width of the front and back faces 13, 14 is greater than the height of the box.

In FIG. 1A, the box 10 has a first set of perforated lines 110, 120. Perforated lines 110 are positioned on the front face 13. The perforated lines 110 are straight and begin from the edge of the front face 13 that is perpendicular to the upper face 11 towards the middle of the front face 13. Perforated lines 120 are positioned on the back face 14. The perforated lines 120 are straight and begin from the edge of the back face 14 that is perpendicular to the lower face 12 towards the middle of the back face 14.

When the perforated lines are torn, flaps 130, 140 are formed and dispensing apertures 150, 160 are provided. A portion of the front face 13 and back face 14 conveniently becomes a hinge.

Also in FIG. 1A, and according to another embodiment, the box 10 has a second set of perforated lines 111, 121.

Perforated lines 111 are positioned on the upper face 11. The perforated lines 111 are straight and begin from the edge of the upper face 11 that is perpendicular to the front face 13 towards the middle of the upper face 11. Perforated lines 121 are positioned on the lower face 12. The perforated lines 121 are straight and begin from the edge of the lower face 12 that is perpendicular to the back face 14 towards the middle of the lower face 12.

When the perforated lines are torn, flaps 131, 141 are formed and additional dispensing apertures 151, 161 are provided. A portion of the upper face 11 and lower face 12 conveniently becomes a hinge.

The dispensing apertures 150, 160, 151, 161 are desirably sized and configured to permit one-at-a-time dispensing of a plurality of gloves. Therefore, the dispensing apertures 150, 160, 151, 161 are positioned on the box 10 to permit reasonably easy access to a user without causing excessive dispensing. It will be understood that the dispensing apertures 150, 160, 151, 161 may assume any other suitable configuration that meet these requirements.

The flaps 130, 140, 131, 141 are used as a means for shielding the dispensing apertures 150, 160, 151, 161 from the entry of contaminants from the surrounding environment. The flaps 40, 41 have a closed position and an open position. In the open position (as shown), the flaps 130, 140, 131, 141 allow a glove to be removed by a user from the box 10 through the dispensing apertures 30, 31.

The problem of unwanted space in the box 10 caused by a stack of gloves may be greatly reduced or eliminated when two stacks of gloves are provided, one stack positioned on each side of a separator. The separator is static. Desirably, a separator allows for separate dispensing through the dispensing apertures 150, 160, 151, 161 associated with each stack.

Figure 2A:
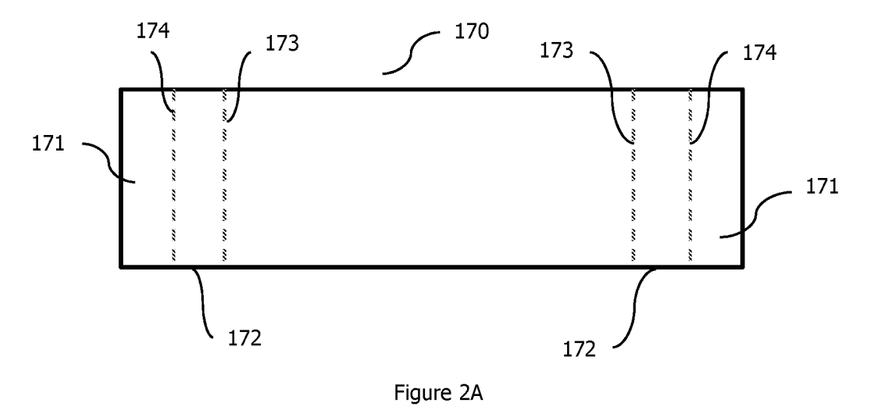
FIG. 2A is a top plan view of a static internal separator when laid flat.

In FIG. 2A, the separator is a single sheet element 170 having inner fold lines 173 and outer fold lines 174.

Figure 3A:
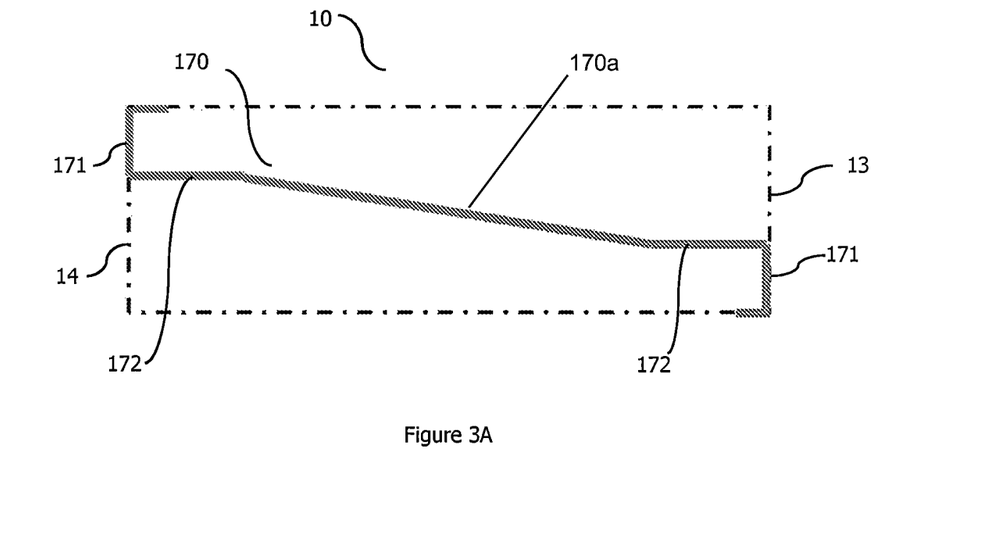
FIG. 3A is a sectional view showing the position of the static internal separator when aligned on a gradient.

In FIG. 3A, the sheet element 170 is bent about the outer fold lines 174, end tabs 171 form at each end of the sheet element 170. Each end tab 171 can be bent up and down. The flat portion 172 between inner fold lines 173 and outer fold lines 174 is used to support the cuffs of the gloves. In a preferred embodiment, one tab is bent upwards while the other tab is bent downwards. The end tabs 171 prevent from upward or downward movement of the internal separator. The height of the end tab 171 when bent about the outer fold lines 174 must be at least of the height as the cuff end of a stack of gloves.

In a preferred embodiment, the end tabs 171 are positioned touching the inside surface of the front and back face 13, 14, forming an inclined slope. To allow for an inclined slope, the total length of the sheet element 170 in FIG. 2A is longer compared to that of the length of the sheet 270 in FIG. 2B. The gradient positioning of the separator 170 (gradient portion 170a) ensures that the gloves slide cuff out first and also prevents the gloves from moving backwards when a glove is withdrawn. Such a configuration is also used to avoid asymmetry. That is, the cuff of each glove is often thicker.

The separator 170 may couple to the box 10 via any known manner, such as, by way of non-limiting example, heat sealing, stapling, adhering via adhesives and so forth. In a preferred embodiment, the separator is not coupled to the box 10 where the separator 170 is simply placed in the box 10 in a snug-fit manner. This reduces manufacturing costs as no coupling components are required.

Figure 4A:
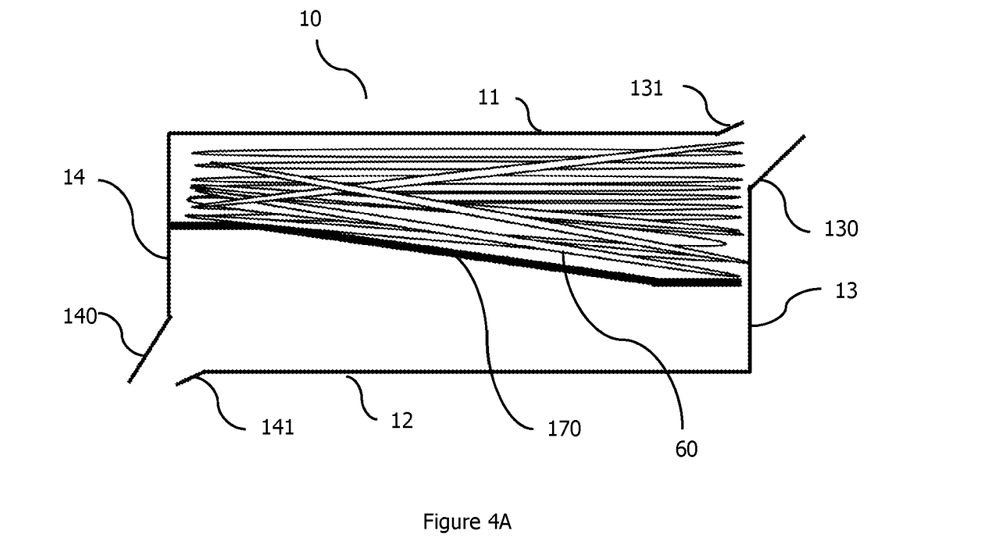
FIG. 4A is a sectional view similar to FIG. 1A, but showing the position of the static internal separator when aligned on a gradient and is fully loaded with gloves positioned on the static internal separator.

In FIG. 4A, a first stack of gloves 60 is placed in the box 10. The first stack 60 is oriented so that the gloves are stacked cuff-to-cuff (or wrist-to-wrist). The cuffs are positioned adjacent to the dispensing aperture 150 of the front face 13. The second stack 61 is also oriented so that the gloves are stacked cuff-to-cuff (or wrist-to-wrist). Each stack of gloves is aligned cuff-to-cuff (or wrist-to-wrist), with the cuffs of each stack is on opposing ends. This is to ensure that the overall thickness of the gloves in the box is symmetrical. The cuffs are positioned adjacent to the dispensing aperture 160 of the back face 14. The single sheet element 170 is positioned between the first and second stacks of gloves 60, 61.

In an embodiment as shown in FIG. 1B, the box 10 includes perforated lines 211 which are positioned on the upper face 11 and perforated lines 221 which are positioned on the lower face 12. When the perforated lines 211, 221 are torn, a dispensing aperture 251, 261 is provided. The perforated lines 211, 221 form a generally oval shape aperture.

In a preferred embodiment, a film 280 having a slit is used as a means for shielding the dispensing apertures 251, 261 from the entry of contaminants from the surrounding environment.

The dispensing apertures 251, 261 is desirably sized and configured to permit one-at-a-time dispensing of a plurality of gloves through the slit. Therefore, the dispensing aperture 251, 261 is positioned on the box 10 to permit reasonably easy access to a user without causing excessive dispensing. It will be understood that the dispensing aperture 30 may assume any other suitable configuration that meet these requirements.

The problem of unwanted space in the box 10 caused by a stack of gloves may be greatly reduced or eliminated when two stacks of gloves are provided, one stack positioned on each side of a separator. Desirably, the separator allows for separate dispensing through the dispensing aperture 251, 261 associated with each stack.

Figure 2B:
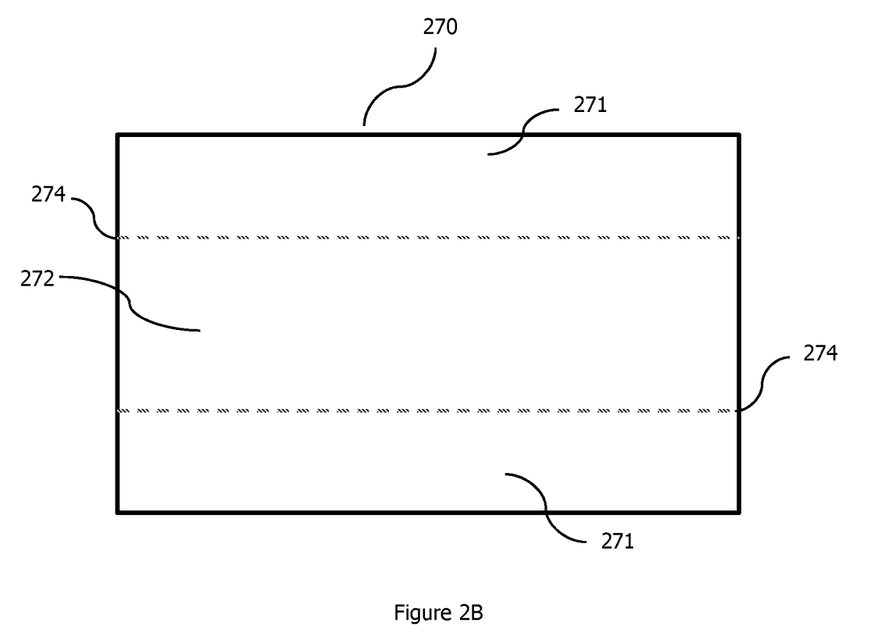
FIG. 2B is a top plan view of a static internal separator when laid flat, in another embodiment.

In FIG. 2B, the separator is static and consists of two sheet elements 270, each sheet element having outer fold lines 274.

Figure 3B:
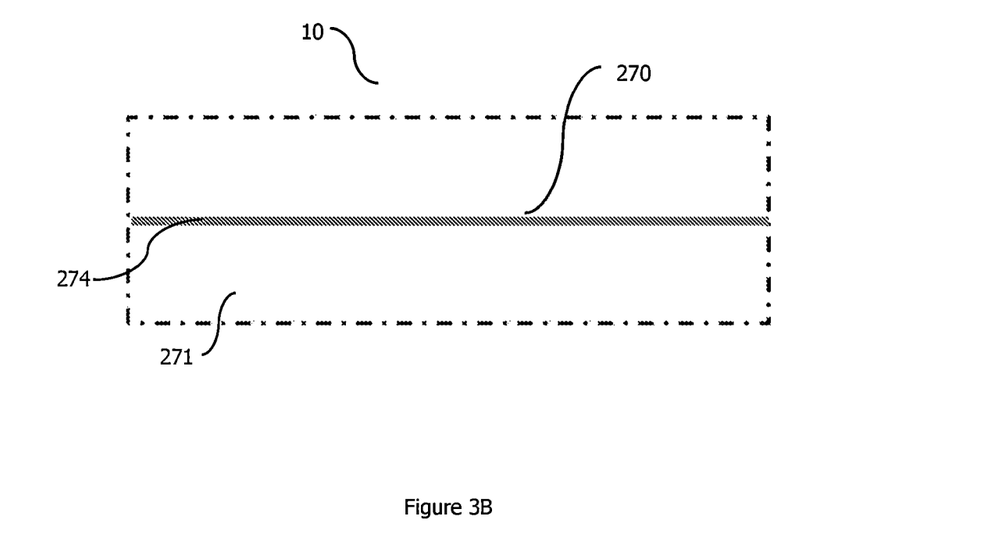
FIG. 3B is a sectional view showing the position of the static internal separators when aligned flat.

In FIG. 3B, each sheet element 270 is bent about the outer fold lines 274, side tabs 271 form on each side of the sheet. Preferably, each sheet element 270 is bent about the outer fold lines 274 in the same direction. The side tabs 271 are positioned touching the inside surface of the side faces 15. The side tabs 271 prevent from upward or downward movement of the she sheets 270. The height of the side tab 271 when bent about the outer fold lines 274 must be at least of the height as the cuff end of a stack of gloves. The flat portions 272 of the sheet elements 270 are placed on top of each other.

The sheet elements 270 may couple to the box 10 via any known manner, such as, by way of non-limiting example, heat sealing, stapling, adhering via adhesives and so forth. In a preferred embodiment, the separator is not coupled to the box 10 where the sheet elements 270 are simply placed in the box 10 in a snug-fit manner. This reduces manufacturing costs as no coupling components are required.

Figure 4B:
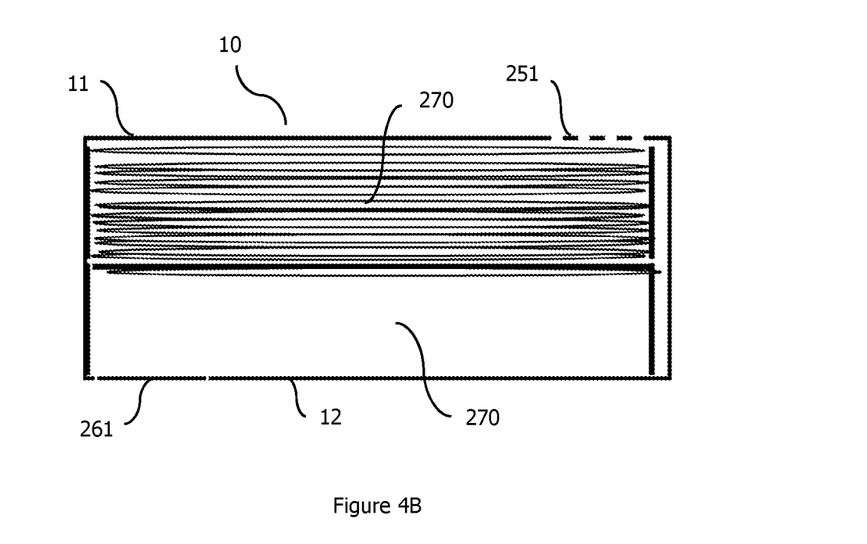
FIG. 4B is a sectional view similar to FIG. 1B, but showing the position of the static internal separator when aligned flat and is fully loaded with gloves positioned on the static internal separator.

In FIG. 4B, a first stack of gloves 60 is placed in the box 10. The first stack 60 is oriented so that the gloves are stacked cuff-to-cuff (or wrist-to-wrist). The cuffs are positioned adjacent to the dispensing aperture 251 of the upper face 11. The second stack 61 is also oriented so that the gloves are stacked cuff-to-cuff (or wrist-to-wrist). The cuffs are positioned adjacent to the dispensing aperture 261 of the lower face 12. Each stack of gloves is aligned cuff-to-cuff (or wrist-to-wrist), with the cuffs of each stack is on opposing ends. This is to ensure that the overall thickness of the gloves in the box is symmetrical. The sheets 270 are positioned between the first and second stack of gloves 60, 61.

In an embodiment, each stack of gloves 60, 61 comprises of fifty gloves. In another embodiment, each stack of gloves 60, 61 comprises of one hundred gloves.

In an exemplary usage of the dispenser in accordance with the invention, gloves are dispensed from one aperture at a time. Once all the gloves have been dispensed from an aperture, the box 10 is turned upside down so that the gloves may be dispensed from the opposing aperture.

The box 10 and the separators 170, 270 may be constructed from any material or combination of materials which permit it to operate as shown and/or described herein. Such materials may include, for example, but not by way of limitation, cardboard, paperboard, plastic, metal, polymer film, and so forth.

It will be understood that the invention may be embodied in ways other than those specifically described without departure from its scope as defined by the claims.

The invention claimed is:

1. A dispenser for gloves comprising:
a box being comprised of a plurality of faces,
wherein said plurality of faces is comprised of two opposing faces,
wherein each opposing face of said two opposing faces is comprised of a corresponding set of perforated lines, and
wherein each corresponding set of perforated lines is tearable so as to form a respective dispensing aperture on each opposing face of said two opposing faces;
two stacks of unfolded gloves disposed in said box, each unfolded glove having a cuff,
wherein each stack of unfolded gloves is orientated in said box so that a respective cuff of each unfolded glove is positioned adjacent to a corresponding dispensing aperture so as to dispense each unfolded glove cuff-first through said corresponding dispensing aperture; and
a static internal separator positioned between the two stacks of unfolded gloves,
wherein said static internal separator is comprised of a single sheet element having end tabs so as to support said static internal separator within said box,
wherein said single sheet element comprises a gradient portion between said end tabs, and
wherein said single sheet element further comprises flat portions, each flat portion being disposed between said gradient portion and a respective end tab so as to place the respective cuff of each unfolded glove on a respective flat portion.

2. The dispenser for gloves of claim 1, wherein said single sheet element comprises fold lines between said gradient portion and said flat portions.

3. The dispenser for gloves of claim 1, wherein said end tabs of said single sheet element are bent in opposing directions.

4. The dispenser for gloves of claim 1, wherein said end tabs of said single sheet element are positioned parallel to a front face of said plurality of faces and a back face of said plurality of faces, said two opposing faces being comprised of said front face and said back face.

5. The dispenser for gloves of claim 1, wherein said plurality of faces is comprised of an additional two opposing faces,
wherein each opposing face of said two opposing faces is comprised of a corresponding set of perforated lines on an upper face and a lower face, said two opposing faces being comprised of said upper face and said lower face,
wherein each opposing face of said additional two opposing faces is comprised of an additional corresponding set of perforated lines on said front face and said back face, said additional two opposing faces being comprised of said front face and said back face,
wherein the corresponding set of perforated lines on said upper face and the additional corresponding set of perforated lines on said front face are tearable so as to form a respective extended dispensing aperture on said upper face and said front face, and
wherein the corresponding set of perforated lines on said lower face and the additional corresponding set of perforated lines on said back face are tearable so as to form an additional respective extended dispensing aperture on said lower face and said back face.

6. The dispenser for gloves of claim 5, wherein each of the corresponding set of perforated lines on said upper face, the additional corresponding set of perforated lines on said front face, the corresponding set of perforated lines on said lower face, and the additional corresponding set of perforated lines on said back face, define a respective flap having a closed position and an open position.

7. The dispenser for gloves of claim 1, wherein said static internal separator is comprised of a second sheet element having second end tabs so as to support said static internal separator within said box.

8. The dispenser for gloves of claim 7, wherein said second sheet element is comprised of a second flat portion, said flat portion being disposed on said second flat portion.

9. The dispenser for gloves of claim 7, wherein said end tabs of said single sheet element are positioned parallel to a front face of said plurality of faces and a back face of said plurality of faces, said two opposing faces being comprised of said front face and said back face, said second end tabs being positioned parallel to said front face and said back face.

\* \* \* \* \*